(12) United States Patent
Clifton et al.

(10) Patent No.: US 11,580,432 B2
(45) Date of Patent: Feb. 14, 2023

(54) SYSTEM MONITOR AND METHOD OF SYSTEM MONITORING TO PREDICT A FUTURE STATE OF A SYSTEM

(71) Applicant: Oxford University Innovation Limited, Oxford (GB)

(72) Inventors: David Andrew Clifton, Oxfordshire (GB); Glen Wright Colopy, Oxfordshire (GB); Marco Andre Figueiredo Pimentel, Oxfordshire (GB)

(73) Assignee: Oxford University Innovation Limited, Oxford (GB)

( * ) Notice: Subject to any disclaimer, the term of this patent is extended or adjusted under 35 U.S.C. 154(b) by 1061 days.

(21) Appl. No.: 16/239,144

(22) Filed: Jan. 3, 2019

(65) Prior Publication Data
US 2019/0156233 A1    May 23, 2019

Related U.S. Application Data

(63) Continuation of application No. PCT/GB2017/052007, filed on Jul. 7, 2017.

(30) Foreign Application Priority Data

Aug. 2, 2016    (GB) ..................... 1613318

(51) Int. Cl.
*G06N 7/00*    (2006.01)
*G06F 17/18*    (2006.01)
(Continued)

(52) U.S. Cl.
CPC ............. *G06N 7/005* (2013.01); *A61B 5/725* (2013.01); *A61B 5/7275* (2013.01); *G06F 17/18* (2013.01);
(Continued)

(58) Field of Classification Search
CPC ...... G16H 50/70; G06F 17/18; G06K 9/6255; G06K 9/00563; G06K 9/00496;
(Continued)

(56) References Cited

U.S. PATENT DOCUMENTS

| 6,381,554 B1 | 4/2002 | Matsuo et al. |
| 2002/0107641 A1 | 8/2002 | Schaeffer et al. |

(Continued)

FOREIGN PATENT DOCUMENTS

| WO | WO 2010/120800 | 10/2010 |
| WO | WO 2005/039388 | 4/2012 |

(Continued)

OTHER PUBLICATIONS

Colopy et al. "Bayesian Optimisation of Personalised Models for Patient Vital-Sign Monitoring." IEEE Journal of Biomedical and Health Informatics 22(2), 2018, pp. 301-310.

(Continued)

*Primary Examiner* — Yaron Cohen
(74) *Attorney, Agent, or Firm* — Levine Bagade Han LLP

(57) ABSTRACT

System monitors and methods of monitoring a system are disclosed. In one arrangement a system monitor predicts a future state of a system. A data receiving unit receives system data representing a set of one or more measurements performed on the system. A first statistical model is fitted to the system data. The first statistical model is compared to each of a plurality of dictionary entries in a database. Each dictionary entry comprises a second statistical model. The second statistical model is of the same general class as the first statistical model and obtained by fitting the second statistical model to data representing a set of one or more previous measurements performed on a system of the same type as the system being monitored and having a known subsequent state. A prediction of a future state of the system (Continued)

being monitored is output based on the comparison. The first statistical model and the second statistical model are each a stochastic process or approximation to a stochastic process.

22 Claims, 2 Drawing Sheets

(51) Int. Cl.
| | | |
|---|---|---|
| *G06K 9/00* | (2022.01) | |
| *G06K 9/62* | (2022.01) | |
| *G16H 50/70* | (2018.01) | |
| *G06V 30/242* | (2022.01) | |
| *A61B 5/00* | (2006.01) | |

(52) U.S. Cl.
CPC ..... *G06K 9/00496* (2013.01); *G06K 9/00563* (2013.01); *G06K 9/6255* (2013.01); *G06K 9/6284* (2013.01); *G06V 30/242* (2022.01); *G16H 50/70* (2018.01)

(58) Field of Classification Search
CPC .. G06K 9/6284; G06K 9/6278; G06K 9/6215; A61B 5/7275; A61B 5/725; G06N 7/005; G06V 30/242
See application file for complete search history.

(56) References Cited

U.S. PATENT DOCUMENTS

| | | |
|---|---|---|
| 2004/0265874 A1 | 12/2004 | Binder et al. |
| 2008/0161652 A1 | 7/2008 | Potts et al. |
| 2012/0041277 A1 | 2/2012 | Ebadollahi et al. |
| 2014/0201126 A1* | 7/2014 | Zadeh ............... A61B 5/165 706/52 |
| 2015/0006456 A1* | 1/2015 | Sudharsan ........... G16H 50/50 706/46 |

FOREIGN PATENT DOCUMENTS

| | | |
|---|---|---|
| WO | WO 2014/207461 | 12/2014 |
| WO | WO 2016/040732 | 3/2016 |

OTHER PUBLICATIONS

Colopy et al. "Likelihood-Based Artefact Detection in Continuously-Acquired Patient Vital Signs", IEEE Engineering in Medicine & Biology Conference, South Korea, 2017, pp. 2146-2149.

Colopy et al.: "Bayesian Gaussian processes for identifying the deteriorating patient", 2016 38th Annual International Conference of the IEEE Engineering in Medicine and Biology Society, IEEE, Aug. 16, 2016, pp. 5311-5314, XP032980363.

Colopy et al: "Bayesian Gaussian processes for identifying the deteriorating patient", PRS Transfer Report, Sep. 6, 2015, pp. 1-51, XP055427492.

Colopy et al: "Bayesian optimisation of Gaussian processes for identifying the deteriorating patient", 2017 IEEE EMBS International Conference on Biomedical & Health Informatics (BHI), IEEE, Feb. 16, 2017, pp. 85-88, XP033084867.

Birrenkott, Drew, "Respiratory Quality Index Design and Validation for ECG and PPG Derived Respiratory Data", PRS Transfer Report, Dec. 11, 2015, pp. 1-58.

Velardo et al.: "Automatic generation of personalised alert thresholds for patients with COPD", 2014 22nd European Signal Processing Conference (EUSIPCO), EURASIP, Sep. 2014, pp. 1990-1994, XP032682043.

* cited by examiner

SYSTEM MONITOR AND METHOD OF SYSTEM MONITORING TO PREDICT A FUTURE STATE OF A SYSTEM

CROSS-REFERENCE TO RELATED APPLICATIONS

This application is a continuation International Patent Application Number PCT/GB2017/052007 filed Jul. 7, 2017, which claims priority to GB Patent Application Number 1613318.3 filed Aug. 20, 2016, the contents of which are incorporated herein by reference in their entireties.

BACKGROUND OF THE INVENTION

The present invention relates to system monitors and methods of system monitoring, particularly for predicting a future state of a system being monitored. The systems are particularly applicable to providing an early warning of a change in a system state, for example a future machine failure or adverse medical event in a human or animal subject.

In clinical settings, and particularly in acute settings such as hospitals, patient data are continually monitored to provide values (e.g. vital signs) relating to a patient's current health. These measurements are of particular importance in intensive care units and other high-dependency units. Measured vital signs may be compared with thresholds and an alarm raised when it is detected that a vital sign is beyond a corresponding threshold.

An improved method over simple vital sign threshold warning is the Modified Early Warning Score (MEWS). MEWS can be calculated for each patient, and considers the abnormality of multiple vital signs. However assessments like MEWS are staff-intensive, and thus not suitable for continuous monitoring. MEWS may be difficult to calculate in the presence of missing information, and MEWS also does not account for vital sign trajectories or signals that are individually healthy but jointly abnormal. Furthermore any manual monitoring or calculation is subject to human error.

An improvement on the above is offered by continuous probabilistic monitoring systems that compare a patient's current set of vital signs to those of a global population of healthy patients. Possibly the best known of these methods is the Parzen window kernel density estimate (KDE). If the observed data stray sufficiently from those previously acquired from a cohort of stable patients (in the example of patient monitoring) then it is a signal of abnormality and potential physiological deterioration. Other probabilistic methods have made use of extreme value theory (EVT) to anticipate whether extreme observations represent a true deterioration, an artefactual measurement, or a reasonably-expected extreme arising from long-periods of continuous monitoring. In essence, these methods replace an absolute threshold with a probabilistic threshold that can account for the correlation between vital signs and lengthy observation periods. Patient risk, though, is still assessed at a single point in time, thereby losing information from previous measurements, and making the inaccurate assumption of independent and identically distributed observations (that is, that the data for the "patient being monitored" have the same probability distribution as the data from the entire population of "patients previously acquired", which were used to form the training set—this is an inaccurate assumption because an individual will have data that are some subset of the data of an entire population). To address the correlated time series nature of data, methods have been suggested to estimate patient trajectories, but these frequently rely on manipulating the data to fit into a specific model, for example into discrete time points.

BRIEF SUMMARY OF THE INVENTION

It is an object of the invention to provide an improved system monitor capable of predicting a future state of a system more accurately, more reliably and/or earlier than current methods. Where the system is a human or animal patient, there is evidence to suggest that earlier responses to medical events can reduce mortality rates and improve patient outcomes.

According to an aspect of the invention, there is provided a system monitor configured to predict a future state of a system being monitored, comprising: a data receiving unit configured to receive system data representing a set of one or more measurements performed on the system; and a processing unit configured to: fit a first statistical model to the system data; compare the first statistical model to each of a plurality of dictionary entries in a database, each dictionary entry comprising a second statistical model, the second statistical model being of the same general class as the first statistical model and obtained by fitting of the second statistical model to data representing a set of one or more previous measurements performed on a system of the same type as the system being monitored and having a known subsequent state; and output a prediction of a future state of the system being monitored based on the comparison, wherein: the first statistical model and the second statistical model are each a stochastic process or approximation to a stochastic process.

Thus, a system monitor is provided which obtains a statistical model (the first statistical model) by performing a fitting of the statistical model to system data derived from measurements performed on the system. The first statistical model thus provides a formal statistical representation of the behaviour of the system based on the system data.

The system monitor then uses the first statistical model to compare the system being monitored to other systems which have been monitored in the past by comparing the first statistical model to second statistical models (plural) in a database, each of the second statistical models being referred to as a "dictionary entry" in the database (the "dictionary"). In this way, the system monitor is able to rapidly and reliably assess a degree of similarity between the system being monitored and the systems that have been monitored in the past and on this basis provide a rapid and reliable prediction of a future state of the system being monitored.

The use of statistical models allows manipulation within a formal probabilistic Bayesian framework, which allows noise and artefact (as are typical in data from patient-worn sensors for example) to be handled in a robust manner, thereby improving overall performance. For example, in the case where the system being monitored is a human patient, the improved overall performance may comprise increased accuracy and a reduction in the number of "false alarms" for patients who are actually in a "normal" or "stable" state. The methodology has been found to outperform heuristic approaches used in alternative known methods.

Furthermore, the use of a statistical model which comprises a stochastic process or approximation to a stochastic process (i.e. a construct which behaves in a similar way to a stochastic process but does not satisfy the formal definition of a stochastic process) allows proper account to be taken of the trajectories of the system data, rather than treating measurement data point by point (i.e. with no account being taken of any of the historical data that have been collected for the same system, for example patient), as is done in manual MEWS methods for example. The inventors have found that the approach works particularly accurately where the stochastic process or approximation to a stochastic process is a Gaussian process or approximation to a Gaussian process.

The inventors have found that the approach can be implemented with particularly high performance (high speed and/or low computing resource requirements) where linear state-space models (also referred to as Kalman filters) are used to provide an approximation to a Gaussian process. The approximation was found to provide similar properties to a true Gaussian process but with about 100× faster operation.

Furthermore, the analysis used by the system monitor involves modelling that is personalised to the system being monitored and does not need to make the typically inaccurate assumption of independent and identically distributed observations, as discussed in the introductory part of the description above.

In the case where the system being monitored is a human or animal, the system monitor is able to exploit the "big data" accumulation of very large numbers of patient multivariate vital-sign data (and, in principle, other time-series data such as the results of daily laboratory tests, etc., as are commonly-acquired in various healthcare settings). The inventors have found that the approach provides significantly increased performance compared with existing methods. In many cases it has been found possible to accurately predict patient deterioration rather than simply identifying patient deterioration as it happens (as is current practice).

The invention is useful for example in the fast-growing domain of wearable sensors, which are currently limited to non-clinical markets because of the lack of robustness for existing methods, described above. It may also be applied to data from video-based monitoring of patients and/or used to improve bed-side patient monitors.

In an embodiment, the plurality of dictionary entries comprises one or more groups of dictionary entries, each group exclusively containing dictionary entries having a common known subsequent state that is different to the known subsequent state of each of the other groups. By determining which group of dictionary entries the first statistical model is most similar to it is possible rapidly and accurately to determine a prediction of a future state of the system.

In an embodiment, the comparison comprises calculating a similarity between the first statistical model and each of the plurality of dictionary entries in the database to obtain respective similarity values. The similarity values provide a convenient basis on which to quantify degrees of similarity between the first statistical model and respective dictionary entries. The inventors have found that calculating the similarity values using the Hellinger distance or Kullback-Leibler divergence is particularly effective.

In an embodiment, the comparison comprises calculating one or more groups of similarity values, each group similarity value representing how similar the first statistical model is to a respective one of the one or more groups of dictionary entries. The prediction of the future state is obtained based on the one or more group similarity values. Each of the one or more group similarity values is calculated using the similarity values obtained for the dictionary entries of the group. In an embodiment, each group similarity value is based on a similarity value representing the dictionary entry that is the $n^{th}$ most similar to the first statistical model in the group of dictionary entries (obtained for example by sorting the entries into ascending order to similarity). Although other approaches are possible, the inventors have found that using the $n^{th}$ most similar dictionary entry is computationally efficient and provides an effective measure of the similarity of the group of dictionary entries as a whole to the first statistical model. The choice of which particular value to choose for n can be tailored to the particular system being monitored and the nature of the system data. The value of n should be sufficiently high to exclude dictionary entries which may be artefactual while at the same time not being so high that too many dictionary entries representing genuinely high degrees of similarity are excluded.

According to an alternative aspect, there is provided a method of monitoring a system in order to predict a future state of the system, comprising using a computer to: receive system data representing a set of one or more measurements performed on the system; fit a first statistical model to the system data; compare the first statistical model to each of a plurality of dictionary entries in a database, each dictionary entry comprising a second statistical model, the second statistical model being of the same general class as the first statistical model and obtained by fitting of the second statistical model to data representing a set of one or more previous measurements performed on a system of the same type as the system being monitored and having a known subsequent state; and output a prediction of a future state of the system being monitored based on the comparison, wherein: the first statistical model and the second statistical model are each a stochastic process or approximation to a stochastic process.

BRIEF DESCRIPTION OF THE SEVERAL VIEWS OF THE DRAWINGS

The invention will be further described by way of example with reference to the accompanying drawings, in which.

DETAILED DESCRIPTION OF THE INVENTION

Embodiments of the invention described below mostly concern cases where the system being monitored is a human or animal (e.g. a human patient) and where time series measurement data is used. It will be understood that the invention is not limited to systems and/or data of these types. The approach may be applied to data which is not time series data and/or to systems which are not humans or animals. For example, the system may alternatively be a jet engine, water pump, computer or imaging system. The data may comprise time series data or data comprising other pairs or groups of indices. Example indices include pixels, distance, location, time, temperature, pressure, speed, voltage, current, power consumption and voxel location. The system monitor may, for example, remotely analyse data from an aircraft engine and predict engine failure earlier than current methods.

Figure 1:
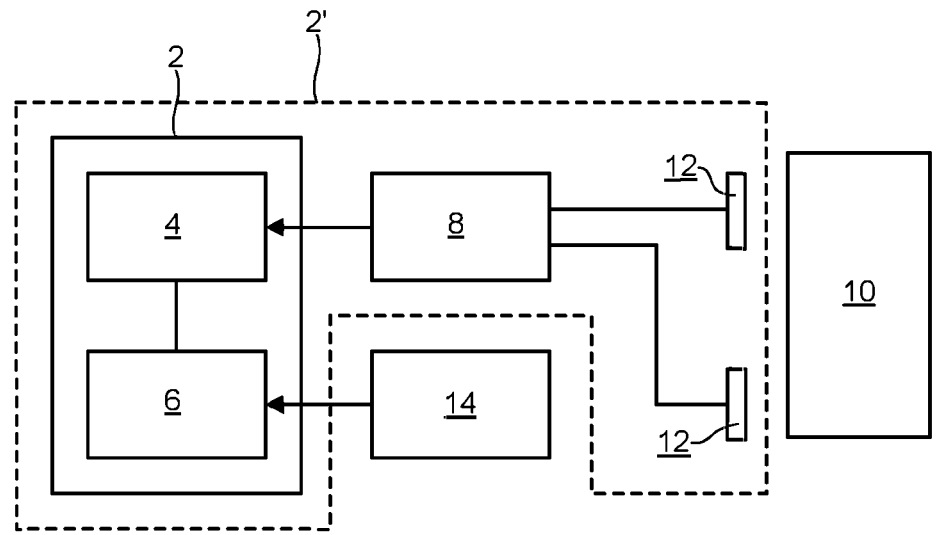
FIG. 1 is a schematic diagram of a system monitor.

FIG. 1 depicts a system monitor 2 according to an embodiment. The system monitor 2 predicts a future state of a system 10 being monitored. The system 10 may be any system, for example a mechanical, electrical, chemical or biological system. The system 10 may be a human or animal. The future state of the system 10 to be predicted may comprise a future deviation from normality, such as breakdown of a machine, when the system is mechanical or electrical, or an adverse medical event, when the system is a biological system. The system monitor 2 can provide warnings to a user about the predicted event, thereby allowing appropriate action to be taken. Embodiments of the invention allow the prediction of the deviation from normality to be made earlier and/or more reliably than alternative manual or automated monitoring techniques.

The system monitor 2 comprises a data receiving unit 4 and a processing unit 6. The data receiving unit 4 receives system data representing a set of one or more measurements performed on the system 10. In the example of FIG. 1 the system data is provided directly by a sensing system 8. The sensing system 8 performs the measurements on the system 10. The sensing system 8 may be provided separately from the system monitor 2 (as depicted by the solid lines in FIG. 1) or may form part of the system monitor (as depicted by the broken line region 2' in FIG. 1). In other embodiments the system data may be provided indirectly, for example via a storage medium that stores system data recorded (e.g. by a sensing system 8 or other means) at a previous time. In other embodiments, all or a portion of the system data is obtained by performing measurements on samples extracted from the system 10. The sensing system 8 may comprise one or more sensors 12 for performing the measurements. The sensors 12 may be configured to act directly on the system 10 and/or on samples extracted from the system 10. For example, in the case where the system 10 is a human or animal the measurements may comprise measurements of one or more of the following: heart rate, respiratory rate, blood oxygenation, systolic blood pressure, diastolic blood pressure, electrocardiogram, blood glucose, temperature, blood constituent levels, pupil size, pain score, Glasgow coma score or any measurements performed on a sample from the human or animal.

In an embodiment, the sensing system 8 is provided in a hospital, in a patient's home or is worn by a patient. The sensing system 8 may send data to the data receiving unit 4 via a network connection (e.g. wired or wireless). In this way a patient's medical condition may be remotely monitored and assessed. The sensing system 8 and/or system monitor 2 (where separate) may include a warning unit to warn the patient or medical staff that the system monitor 2 has predicted a future medical event requiring action. The warning unit may be configured to contact emergency personnel automatically when a negative patient outcome is predicted.

The data receiving unit 4 provides the system data to the processing unit 6. The processing unit 6 fits a first statistical model to the system data. The processing unit 6 then compares the first statistical model to each of a plurality of dictionary entries in a database 14. In the example of FIG. 1 the database 14 is shown outside of the system monitor 2, provided for example via an external storage medium or external data connection (to a server for example). The database may alternatively or additionally be stored locally on the system monitor 2.

Each dictionary entry comprises a second statistical model. The second statistical model is of the same general class as the first statistical model (e.g. a Gaussian process). The second statistical model is obtained by fitting the second statistical model to data representing a set of one or more previous measurements performed on a system of the same type as the system 10 being monitored and having a known subsequent state. For example, the dictionary entries may comprise second statistical models fitted to historical data (representing one or more previous measurements) from patients where a subsequent state of the patient (outcome) has been recorded. (One model is fitted to each separate patient's data, in this example.) The subsequent state may be a binary (positive/negative) outcome, such as whether or not the patient died or had to be re-admitted to an intensive care unit (ICU), or a wider range of subsequent states may be recorded. The subsequent state may comprise one or more of the following for example: tachycardia, bradycardia, tachypnoea, bradypnoea, hypotension, hypertension, hypothermia, hyperthermia, cardiovascular accident, transient ischemic attack, myocardial infarction, infection, pneumonia, atrial fibrillation, shock or death. Alternatively or additionally, the dictionary entries may comprise second statistical models fitted to historical data from healthy individuals or patients who did not suffer any adverse outcome subsequent to the measurements providing the data.

Each dictionary entry thus provides a statistical model derived from another system at a previous time. The comparison between the first statistical model and the dictionary entries may thus be used to determine how similar the system being monitored is to various other systems monitored in the past and whose subsequent states were recorded. The processing unit 6 uses this comparison to determine a prediction of a future state of the system 10 and provides an output of the prediction as information to the user.

The first statistical model and the second statistical model are each a stochastic process or approximation to a stochastic process, for example a Gaussian process or approximation to a Gaussian process. Stochastic processes offer several advantages over other regression models used in the past in this context. For example, they do not impute a functional form relating the dependent variables to the regressor. Pre-specified functional forms can include those meant to handle non-linearity (e.g. polynomial, fractional-polynomial, or Poisson regression) or to specify the extent to which previous observations affect future observations (e.g. models with autoregressive or moving-average components). Such pre-defined functional forms lead to inherent challenges in the modelling process. Most obviously, the pre-specified model may be mis-specified and deviate significantly from the actual form of the generative process, especially where data are absent or sparse. This is especially relevant in a patient-monitoring framework, in which poorly-synchronised monitoring devices may likely contain errors in the times of the recorded measurements, creating temporal uncertainty. This is especially true in mobile or home patient-monitoring where information might be relayed between multiple devices. A simple example could be for the Bluetooth connection of a monitoring device becoming disconnected or desynchronised from other devices being used to monitor the same patient. Stochastic processes (e.g. Gaussian processes) can be designed to accommodate this uncertainty. Stochastic processes are also more immune to drift or bias in the observations than other statistical models. These factors provide improved resilience to drift, bias, incomplete data and temporal uncertainty relative to alternative approaches.

Fitting of stochastic processes such as Gaussian processes to measurement data generally (e.g. time series data) is well known in the art and within the common general knowledge of the skilled person in this technical area. Fitting of approximations to stochastic processes, for example an approximation to a Gaussian process using a linear state-space model (or Kalman filter), to measurement data is also known in the art and within the common general knowledge of the skilled person in this technical area.

In an embodiment the plurality of dictionary entries comprises one or more groups of dictionary entries. Each group exclusively contains dictionary entries having a common known subsequent state that is different to the known subsequent state of each of the other groups. Where there is a plurality of groups of dictionary entries the comparison may comprise determining which of the plurality of groups the first statistical model is most similar to. The prediction of the future state may then be made based on the subsequent state that is common to the dictionary entries in the group that the first statistical model is most similar to. For example, if the first statistical model is found to be most similar to dictionary entries in a group containing dictionary entries for healthy human subjects (characterized by having no recorded negative subsequent outcome), and the other one or more groups contain dictionary entries for patients with negative future states, it may be deduced that the future state of the subject being monitored is likely to be positive. No alarm needs to be raised. When the converse is true, an alarm may be needed.

Figure 2:
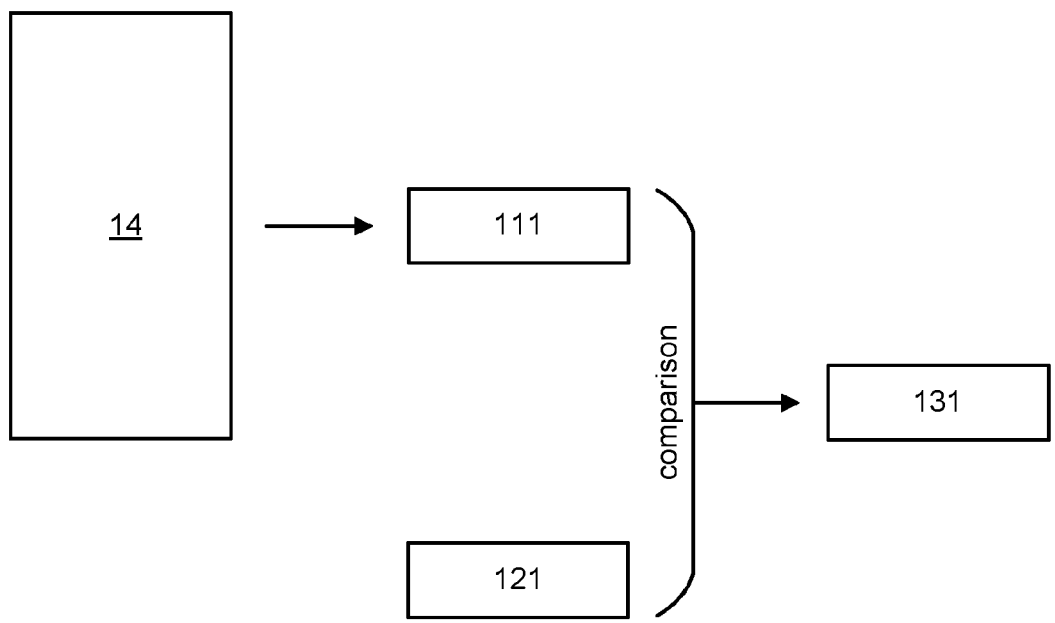
FIG. 2 is a schematic diagram representing comparison between a first statistical model and a group of dictionary entries to obtain a group similarity value.
Figure 3:
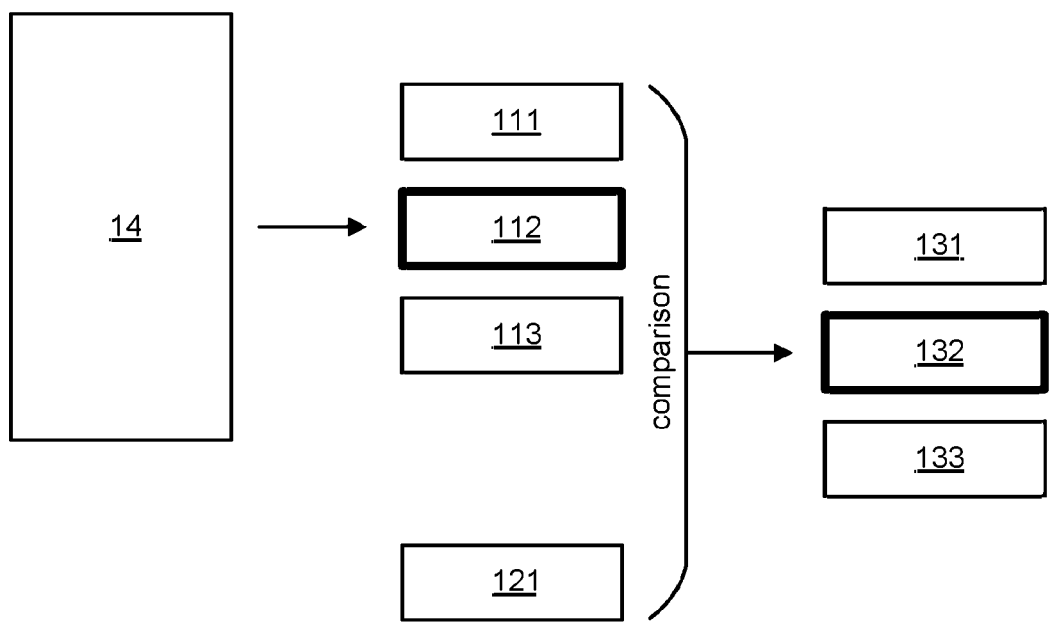
FIG. 3 is a schematic diagram representing comparison between a first statistical model and plural groups of dictionary entries to obtain plural group similarity values.

In an embodiment, the comparison comprises calculating one or more group similarity values. The approach is illustrated schematically in FIGS. 2 and 3. Each group similarity value represents how similar the first statistical model is to a respective one of the one or more groups of dictionary entries. The prediction of the future state may then be obtained based on the one or more group similarity values. For example, in the case where there is just one group 111 of dictionary entries extracted from the database 14, as depicted schematically in FIG. 2, the prediction may be based on whether or not the group similarity value 131, obtained by comparing the group 111 to the first statistical model 121, is above or below a predetermined threshold. Thus, if the group similarity value 131 indicates that the first statistical model 121 is sufficiently similar to dictionary entries of the group 111, it may be deduced that a future state of the system 10 being monitored will be the same as the future state of the systems from which the dictionary entries of the group 111 were derived. In the case where there are plural groups of dictionary entries 111-113, as depicted schematically in FIG. 3, with three group similarity values 131-133 being derived respectively from the three groups of dictionary entries 111-113, the group 112 (for example) having the group similarity value 132 representing the highest similarity between the first statistical model 121 and dictionary entries within the group 112 may be identified as the most similar group and it may be deduced that a future state of the system 10 being monitored will be the same as the future state of the systems from which the dictionary entries of that group 112 were derived.

In an embodiment, the comparison comprises calculating a similarity between the first statistical model and each of the plurality of dictionary entries in the database to obtain respective similarity values (i.e. one similarity value per dictionary entry). Various methods are known for quantifying similarity or lack thereof (e.g. functional distance) between statistical models. In an embodiment, the similarity values are calculated based on the Hellinger distance or Kullback-Leibler divergence. Unlike other comparison methods, which may not model the uncertainty if both time series are inherently stochastic, Kullback-Leibler divergence accounts for dissimilarity between two distributions. Kullback-Leibler divergence is therefore particularly well suited for examining the similarity between stochastic processes such as Gaussian processes. The similarity values provide an efficient basis for quantifying how similar the first statistical model is to each of the dictionary entries being considered.

In the case where group similarity values are calculated for one or more groups of dictionary entries, the one or more group similarity values may each be calculated using the similarity values obtained for the dictionary entries of the group.

The inventors have found that one particularly efficient way of deriving a group similarity value in each group is to base the similarity value on the dictionary entry that is the nth most similar to the first statistical model in the group of dictionary entries. The inventors have found that this approach works particularly well when n is an integer greater than 3, for example an integer in the range of 3 to 10, optionally 3 to 7, optionally 4 to 6, optionally 5, particularly when the system is a biological system (e.g. a human or animal).

Alternatively or additionally, each group similarity value may be calculated using an averaging process over the similarity values of the group. The averaging process may comprise calculating a raw average (e.g. arithmetic mean) of the similarity values. Alternatively or additionally, the averaging process may comprise filtering or weighting steps to remove or down-weight similarity values likely to be anomalous or artefactual and/or to otherwise take into account knowledge about the sensing system 8 and/or systems used to create the dictionary entries.

In an embodiment, the system data comprises time series data. In an embodiment, the fitting of the first statistical model is performed on a windowed version of the system data. The length of the time window is equal to a length of a time window used to fit the second statistical model for each of the dictionary entries. This facilitates meaningful comparison between the first statistical model and the dictionary entries.

In an embodiment, the processing unit 6 is further configured to select a subset of dictionary entries in the database to obtain the plurality of dictionary entries to be used in the comparison. This allows dictionary entries to be selected that are likely to provide the most useful information about the particular system 10 being monitored, for example because the systems corresponding to the dictionary entries are most suitable for comparison with (e.g. because they are most similar to) the system 10 being monitored. Various criteria may be used to select the subset of dictionary entries. These may include one or more of the following for example: patient gender, patient location, patient ethnicity, patient age, patient medical history, patient symptoms, patient medication, patient admission time, procedures performed on patient, patient family history, patient social history, patient travel history, time of physiological measurements, window start time. In one particularly preferred embodiment, the selecting is performed based on a time at which the measurements represented by the data for the fitting of the second statistical model for each dictionary entry was obtained, relative to a time of admission of the human patient to a medical facility. The inventors have found that there is a particularly strong correlation between this factor and patient outcome, such that selecting a subset of dictionary entries using this factor significantly improves the accuracy of predictions of the future state of the system (e.g. prediction of a future medical event). The patients being compared to each other are generally in a more similar situation to each other.

Figure 4:
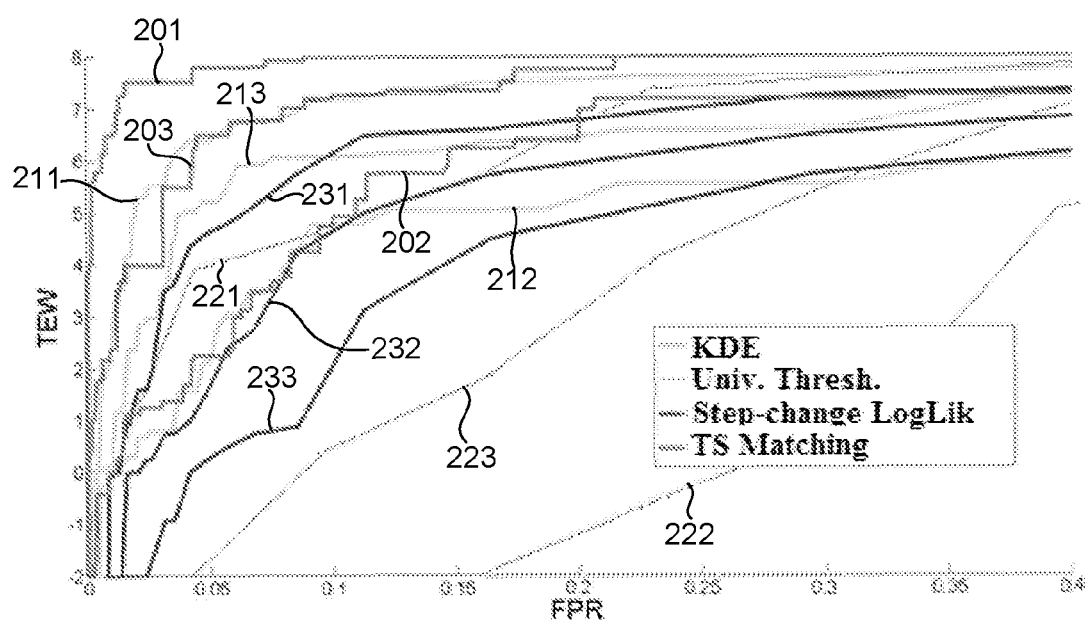
FIG. 4 is a graph comparing the performance of a method according to an embodiment with alternative methods.

FIG. 4 is a graph comparing the performance of a method (marked "TS Matching") of predicting the future state of the system according to an embodiment, in the case where the system is a human patient, with alternative methods "KDE" (standing for kernel density estimate), "Univ. Thresh." (standing for univariate threshold model), and "Step-change LogLik" (standing for step-change log likelihood).

Each method is represented by three curves having the same colour (shading) and respectively representing the first, second and third quartile values for the method. The curves for the method of an embodiment (TS Matching) are marked 201-203; for KDE, the curves are marked 211-213; for Univ. Thresh., the curves are marked 221-223; and for Step-change LogLik, the curves are marked 231-333.

The curves show variations of time of early warning (TEW) in hours against false positive rate (FPR) for the four different methods (first, second and third quartiles for each). In each method, the three curves are obtained by varying a sensitivity of the method. Thus, where the sensitivity is set relatively low the FPR is lowered but the TEW also becomes lower. As the sensitivity is raised the methods generally provide a warning at an earlier time (higher TEW) but the FPR also increases. The curves thus compare not only a model's accuracy (represented by FPR), but also how far into the future a model can accurately predict a future event (represented by TEW). False positive rate is of particular importance in clinical settings, because it is common for patient monitors for example to be required not to have any false positive readings at all during relatively long minimum time periods (e.g. 30 days).

The curves 221-223 representing the univariate threshold model approach are generally lower and/or to the right of the other curves, representing generally lower performance. An example of such a model is one which monitors whether patient vital signs are outside predetermined limits, such as the MEWS method mentioned earlier.

The curves 231-233 representing the step-change log-likelihood model is the next worst, followed by the curves 211-213 representing the kernel density estimate approach.

The best results are provided by the method of an embodiment, as represented by curves 201-203. It is clear from the figure that not only does the method of an embodiment result in far fewer false positives than the other methods, but that it additionally allows a much greater warning time of a future event. This increased performance is particularly impressive given that the particular embodiment is based on using a Gaussian process defined with one variable, whereas the kernel density estimate method uses five variables. A greater warning time of a future event enables improved patient prioritisation, allows clinicians to minimise the impact of adverse medical events and improves patient outcomes.

We claim:

1. A system monitor configured to predict a future state of a system being monitored, comprising:
    a data receiving unit configured to receive system data representing a set of one or more measurements performed on the system; and
    a processing unit configured for:
        obtaining a first statistical model of the system data by fitting the first statistical model to the system data;
        obtaining a comparison of the first statistical model to each of a plurality of dictionary entries in a database, each dictionary entry comprising a second statistical model, the second statistical model being of the same general class as the first statistical model and obtained by fitting of the second statistical model to data representing a set of one or more previous measurements performed on a system of a same type as the system being monitored and having a known subsequent state; and
        outputting a prediction of a future state of the system being monitored based on the comparison, wherein:
    the first statistical model and the second statistical model are each a stochastic process or approximation to a stochastic process;
    the plurality of dictionary entries comprises a plurality of groups of dictionary entries, each group exclusively containing dictionary entries having a common known subsequent state that is different to the known subsequent state of each other group; and
    the comparison comprises determining which of the plurality of groups the first statistical model is most similar to.

2. The system monitor of claim 1, further comprising a sensing system for performing the one or more measurements on the system.

3. The system monitor of claim 1, wherein the stochastic process or approximation to a stochastic process is a Gaussian process or approximation to a Gaussian process.

4. The system monitor of claim 3, wherein the stochastic process or approximation to a stochastic process is an approximation to a Gaussian process using a linear state-space model or Kalman filter.

5. The system monitor of claim 1, wherein the system data is time series data.

6. The system monitor of claim 5, wherein the fitting of the first statistical model is performed on a windowed version of the system data, and the length of a time window of the windowed version is equal to a length of a time window used for the fitting of the second statistical model for each of the dictionary entries.

7. The system monitor of claim 1, wherein the system is a biological system.

8. The system monitor of claim 1, wherein the system is a human or animal.

9. The system monitor of claim 8, wherein the measurements comprise measurements of one or more of the following: heart rate, respiratory rate, blood oxygenation, systolic blood pressure, diastolic blood pressure, electrocardiogram, blood glucose, temperature, blood constituent levels, pupil size, pain score, Glasgow coma score or any measurements performed on a sample from the human or animal.

10. The system monitor of claim 1, wherein the processing unit is further configured for a selecting of a subset of dictionary entries in the database to obtain the plurality of dictionary entries to be used in the comparison.

11. The system monitor of claim 10, wherein the system is a human patient and the selecting is performed based on a time at which the measurements represented by the data for the fitting of the second statistical model for each dictionary entry was obtained, relative to a time of admission of the human patient to a medical facility.

12. The system monitor of claim 1, wherein the comparison comprises calculating group similarity values, each group similarity value representing how similar the first statistical model is to a respective one of the groups of dictionary entries, and where the prediction of the future state is obtained based on the group similarity values.

13. The system monitor of claim 1, wherein the comparison comprises calculating a similarity between the first statistical model and each of the plurality of dictionary entries in the database to obtain respective similarity values.

14. The system monitor of claim 13, wherein each similarity value is calculated based on a Hellinger distance or Kullback-Leibler divergence.

15. The system monitor of claim 13, wherein:
the comparison comprises calculating group similarity values, each group similarity value representing how similar the first statistical model is to a respective one of the groups of dictionary entries and the prediction of the future state is obtained based on the group similarity values, wherein
each of the group similarity values is calculated using the similarity values obtained for the dictionary entries of the group.

16. The system monitor of claim 15, wherein the comparison comprises determining which of the plurality of groups the first statistical model is most similar to using the group similarity values.

17. The system monitor of claim 15, wherein each group similarity value is based on a similarity value representing the dictionary entry that is an $n^{th}$ most similar to the first statistical model in the group of dictionary entries.

18. The system monitor of claim 17, wherein n is an integer greater than 3.

19. The system monitor of claim 17, wherein each group similarity value is calculated using an averaging process over the similarity values of the group of dictionary entries.

20. A method of monitoring a system in order to predict a future state of the system, comprising using a computer to:
receive system data representing a set of one or more measurements performed on the system;
obtain a first statistical model of the system by fitting the first statistical model to the system data;
compare the first statistical model to each of a plurality of dictionary entries in a database, each dictionary entry comprising a second statistical model, the second statistical model being of the same general class as the first statistical model and obtained by fitting of the second statistical model to data representing a set of one or more previous measurements performed on a system of the same type as the system being monitored and having a known subsequent state; and
output a prediction of a future state of the system being monitored based on the comparison, wherein:
the first statistical model and the second statistical model are each a stochastic process or approximation to a stochastic process;
the plurality of dictionary entries comprises a plurality of groups of dictionary entries, each group exclusively containing dictionary entries having a common known subsequent state that is different to the known subsequent state of each other group; and
the comparison comprises determining which of the plurality of groups the first statistical model is most similar to.

21. The method of claim 20, further comprising performing the one or more measurements on the system.

22. A computer program product comprising computer readable code adapted to cause the computer to perform the method of claim 20.

* * * * *